United States Patent [19]

Chung

[11] Patent Number: 5,116,223
[45] Date of Patent: May 26, 1992

[54] SWING ARM FOR SUPPORT OF DENTIST'S SUCTION PUMP NOZZLE

[76] Inventor: Won-Young Chung, No. 310-1501 Hyundai Apt., 484 Kwangjang-dong, Seongdong-ku, Seoul, Rep. of Korea

[21] Appl. No.: 739,165

[22] Filed: Aug. 1, 1991

[30] Foreign Application Priority Data

Jan. 29, 1991 [KR] Rep. of Korea ............. 1278/1991

[51] Int. Cl.⁵ .............................................. A61C 15/00
[52] U.S. Cl. ........................................................ 433/79
[58] Field of Search ................... 433/77, 78, 79, 91, 433/92, 93, 94, 95, 96

[56] References Cited

U.S. PATENT DOCUMENTS 3,346,957 10/1967 Maurer et al. ........................ 433/79
3,445,934  5/1969 Harris .................................... 433/79
3,805,388  4/1974 Kato ...................................... 433/79

*Primary Examiner*—Cary E. O'Connor
*Attorney, Agent, or Firm*—Foley & Lardner

[57] ABSTRACT

A swing arm for supporting a saliva suction pump nozzle which can be maneuvered by an operator without an assistant, consisting of an upper arm and forearm made of lengths of pipe and connected together by a pivotal joint like an elbow, with cables and hose which pass through the forearm and the upper arm being stowed under the surface of the forearm and the upper arm except for the area of said the joint, a vertical part of the upper arm being inserted revolvably in a shaft-supporting holder in the form of a cut of pipe fixed on a pole of a dental chair unit by a two part band, with a saliva suction pump nozzle being fixed on the free end of the suction pump hose at the free end of the forearm.

1 Claim, 2 Drawing Sheets

SWING ARM FOR SUPPORT OF DENTIST'S SUCTION PUMP NOZZLE

FIELD OF INVENTION

The present invention relates to a swing arm for support of the saliva suction pump nozzle, the swing arm to be fixed to the pole of a dental chair's instruments board.

In particular, the present invention relates to a swing arm to support the saliva suction pump nozzle, which will help a dentist while at work to remove the saliva and dental dust from inside the patient's mouth easily and quickly by its smooth maneuverability in all directions.

PRIOR ART

It is observed that, while the dentist treats a patient, saliva wells up while water applied to cool the heat from the friction of grinder and drill cutting, boring or scaling infected parts of teeth and water poured for washing inside the mouth accumulates. Unless this saliva and water with dental dust is sucked up effectively, it follows that not merely the patient under treatment is greatly discomforted but the dentist's work is itself badly hampered.

Usually, this task of removing the saliva and water from inside a patient's mouth is almost entirely entrusted to the nurse in attendance. But this sharing of work in tandem, by which the dentist performs the treatment and the nurse removes the saliva and water, costs more time than otherwise in treatment of patients per person, and is tiring to the team all the more. Because the nurse, moreover, has to take especial care to put the saliva suction pump nozzle in the mouth of the patient under treatment, to the right place each time, without disturbing the dentist's work and has to keep standing on one side of the patient with the nozzle in hand throughout the treatment, her share of duty is a regular ordeal, nothing else possibly to be done while being engaged this way.

SUMMARY OF INVENTION

The inventor, himself with a many long years experience in dental treatment of patients, has long since tried to work out a way of solving this problem, and has finally come to introduce a solution in the present invention.

The objective of the present invention is, in short, to provide an efficiently maneuverable swing arm which holds the saliva suction pump's nozzle close at hand, so that the dentist himself can use it to remove the patient's mouth the saliva and water accumulating in with ease and rapidity each moment it becomes necessary during his treatment.

The swing arm in the present invention is made of two lengths of pipe, connected to each other with a functioning joint. On one end, which is the free end also, of the first length of the pipe is fixed the nozzle of the pump for sucking the saliva in. This nozzle is for a one-time use, and is therefore made to be fitted on the end of the pump hose with ease, its removal after use being equally easy.

This first of the two lengths of pipe, that is, the forearm section, is so constructed and connected to the second of the two by a special joint as to be allowed to bend both laterally and vertically and stay in a desired position, while the other, farther end of the second length of pipe, that is the upper-arm section, is inserted steadily but revolvably in the arm-holding piece of a pipe, which arm-holding is fixed by a two-part band tightly to the pole of a dental chair unit.

In the forearm section, a power switch is fixed near the free end, which can turn the current to the motor of the suction pump on or off as desired.

Owing to a swing arm designed and set up in this fashion, the dentist can empty the patient's mouth of the accumulated saliva and water both easily and speedily the moment it becomes necessary, all without the assistance of a nurse, during his treatment of the patient.

PREFERRED EMBODIMENT

Figure 1:
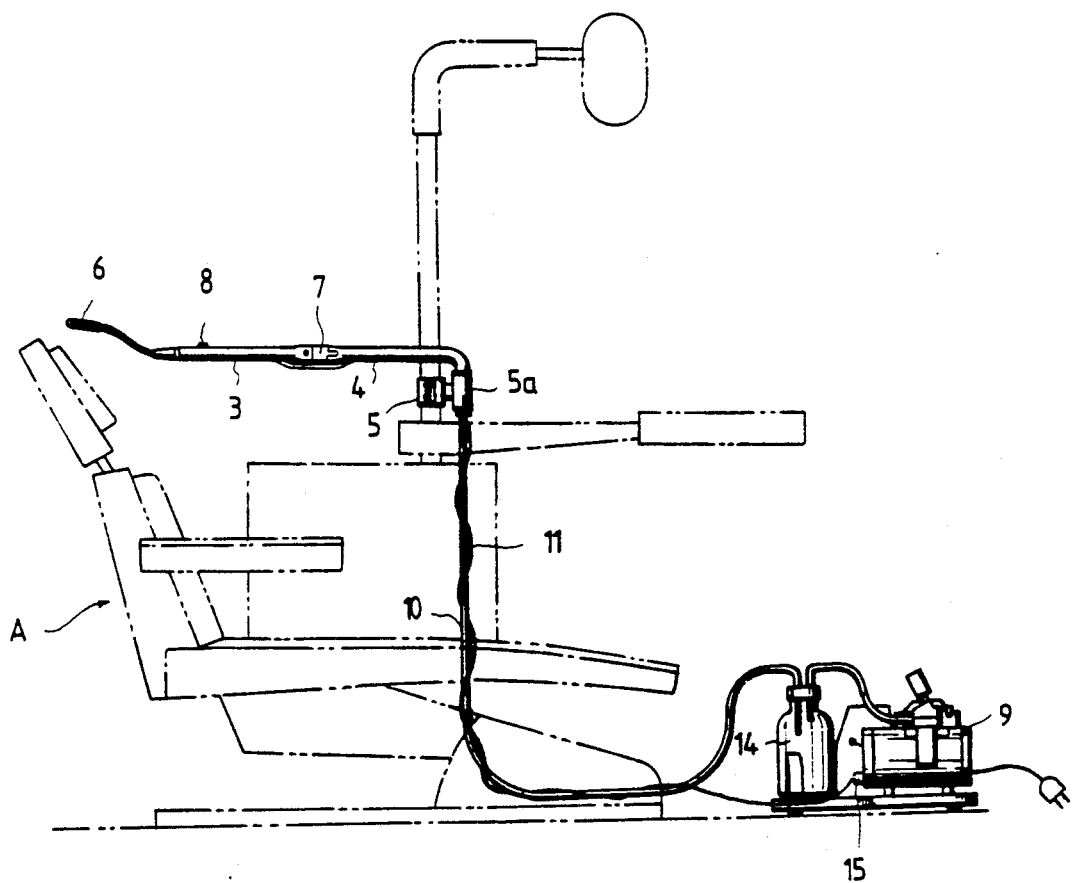
FIG. 1 is a side-view illustration of the swing arm of the present invention for support of the saliva suction pump nozzle installed on a dental chair.
Figure 4:
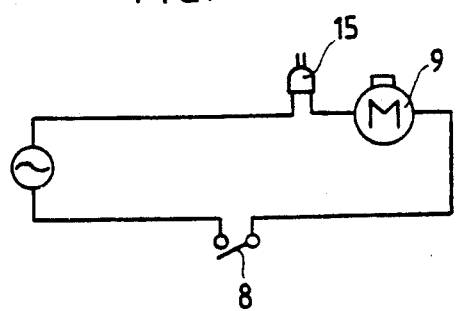
FIG. 4 the power circuit of the suction pump motor related to the present invention.

A detailed description of the present invention will be given below by means of presenting a very much preferred embodiment and also, with reference to the drawings:

In a conventional dental chair unit (A), as is seen in FIG. 1, there stands a pole 1 supporting a board (not shown) on which dental instruments are placed, beside an arm rest. The swing arm 2 of the present invention is fixed to said pole 1.

Figure 2:
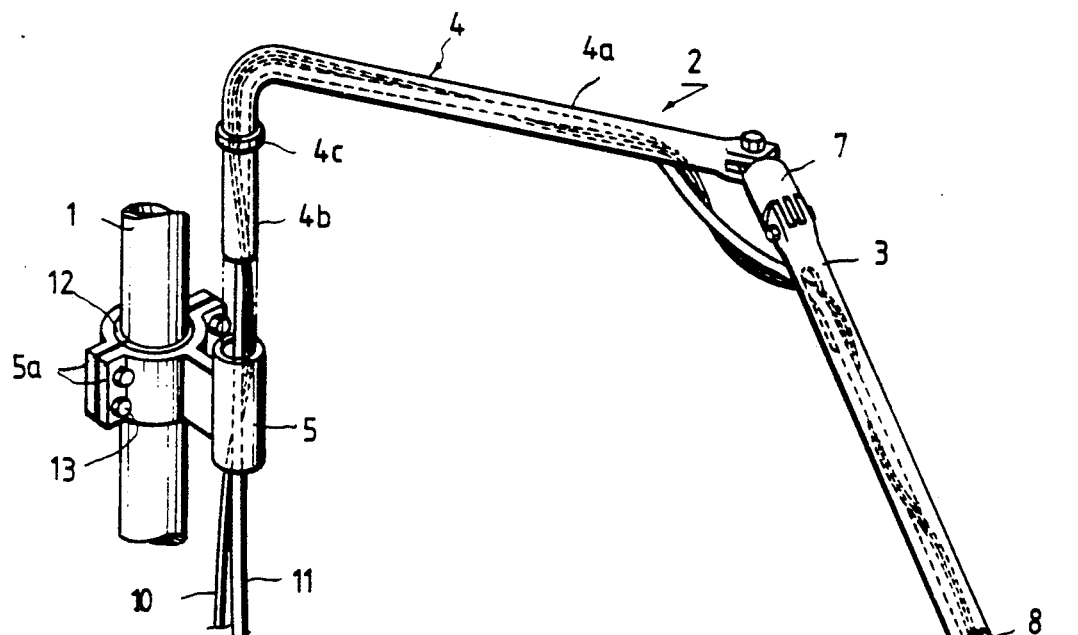
FIG. 2 is a perspective of the swing arm-holder, along with the swing arm separated therefrom, of the present invention.
Figure 3:
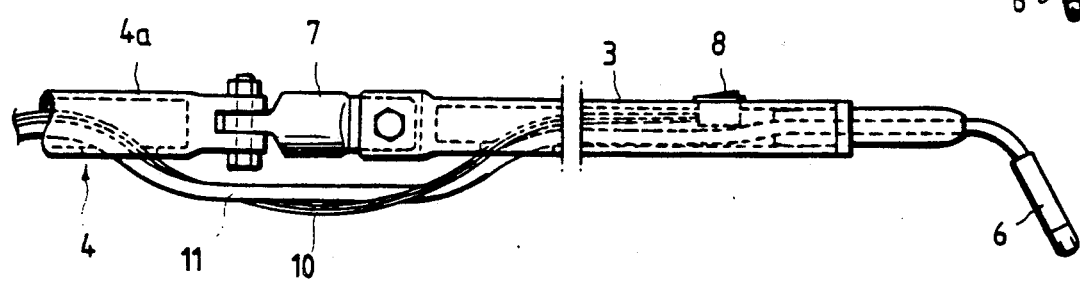
FIG. 3 a partial perspective of the swing arm of the present invention.

As is seen in FIG. 2 said swing arm 2 consists of a forearm 3 and an upper arm 4, both made of lengths of pipe, and a support 5 or holder, a cut of pipe to hold said swing arm 2 revolvably which is inserted in it.

On the free end of said forearm 3 is fixed a saliva suction pump nozzle 6, and the other end of said forearm 3 is connected with the free end of said upper arm 4 by a joint 7. And on the upper surface of said forearm 3 is fixed a power switch 8 near the free end.

Said power switch 8 is electrically connected with one of the cables which connect the power source and the suction pump motor 9, that single cable being led into said swing arm 2, to turn the current to said suction pump motor 9 on or off. Said power switch 8 is turned on each time emptying a patient's mouth of saliva is to be done and is turned off to stop said motor 9 when the emptying is finished.

Meanwhile, said upper arm 4 is fashioned of a length of pipe bent at a right angle, the lateral part 4a of which is attached at its free end to the rear part of said joint 7. The connection of the free end of said lateral part 4a of said upper arm 4 and the rear end of said joint 7 is formed in a manner to allow, as a hinge acts, the lateral swing of said forearm 3 at the rear end of said joint 7. The connection of the rear end of said forearm 3 with the front end of said joint 7 is also in a manner of a hinge, but this is formed in a way to allow the swing of said forearm 3 to move up and down. Thus, owing to this particular way of connection by hinges on said joint 7, said forearm 3 is able to swing both horizontally and vertically at the same time.

The vertical part 4b of said upper arm 4 acts as a shaft for insertion of said swing arm 2 revolvably in a shaft support or holder 5, and especially the part below a collar 4c performs this function as a shaft.

The cables 10 and hose 11 are all stowed away inside said forearm 3 and upper arm 4 of swing arm 2 except at the area which said joint 7 occupies, to make the general appearance of said swing arm 2 neat and tidy.

As said above, said upper arm 4 is inserted revolvably in said shaft support 5, fixed to said pole 1 of a dental chair unit, using said vertical part 4b as a shaft, and thus said swing arm 2 can be swung from left to right and back with said shaft support 5 as a pivot, which lateral swing of said upper arm 4, together with the double function of said joint 7 permitting a swing of said forearm 3 up and down and right and left, facilitates maneuver of said nozzle 6 so that the dentist can bring it to a desired height and position to insert it into the mouth of a patient under treatment at the very desired spot, and remove it with ease and in safety.

Next, about said shaft support 5. It has a two-part band 5a. Owing to said two-part band 5a it is possible to set said shaft support 5 to said pole 1, or separate it, or adjust its position on said pole 1, all as is desired. A pad 12 inside said two-part band 5a from moving, sliding or slipping away, up or down said pole 1, but makes it stay fast, after said shaft support 5 is fixed to it. The two parts of said two-part band 5a are fastened together by bolts 13.

As has been described in detail above, the swing arm for support of a saliva suction pump nozzle of the present invention, can be fixed with ease on the pole which supports the board holding dental instruments of the conventional dental chair unit, to help the dentist empty the patient's mouth of saliva during the treatment speedily and with ease without relying upon the assistance of a nurse in attendance.

Numbers 14 and 15 in the drawings indicate the saliva bottle and a plug respectively.

While the invention has been particularly shown and described with reference to a preferred embodiment thereof, it will be understood by those skilled in the art that some changes in from and details can be made therein without departing from the spirit and scope of the invention.

I claim:

1. A swing arm for supporting a saliva suction pump nozzle, consisting of an upper arm and a forearm made of lengths of pipe and connected together by a joint which acts as a pivot, permitting said forearm to swing up and down, left and right, with cables and hose which pass through said forearm and said upper arm being stowed under the surface of said forearm and upper arm except for the area of said joint, a vertical part of said upper arm being inserted revolvably in a shaft supporting holder in the form of a cut of pipe fixed on a pole of a dental chair unit by a two-part band, with said saliva suction pump nozzle being fixed on a free end of said suction pump hose at the free end of said forearm.

* * * * *